United States Patent
Gittleman

[11] Patent Number: 5,897,320
[45] Date of Patent: Apr. 27, 1999

[54] HYDROSTATIC PRESSURE RELIEVED ABUTMENT POST

[76] Inventor: Neal B. Gittleman, 99 N. Post Oak La., Apt. 420S, Houston, Tex. 77027

[21] Appl. No.: 08/896,303

[22] Filed: Jun. 28, 1997

Related U.S. Application Data

[63] Continuation-in-part of application No. 08/730,933, Oct. 15, 1996, which is a continuation-in-part of application No. 08/374,933, Jan. 18, 1995, Pat. No. 5,564,928.

[51] Int. Cl.⁶ .................................................... A61C 13/12

[52] U.S. Cl. .......................... 433/180; 433/172; 433/218

[58] Field of Search ..................................... 433/172, 173, 433/180, 218, 219

[56] References Cited

U.S. PATENT DOCUMENTS

| | | | |
|---|---|---|---|
| 3,487,544 | 1/1970 | Weissman | 433/218 |
| 5,002,489 | 3/1991 | Fischer et al. | 433/218 |
| 5,564,928 | 10/1996 | Gittleman | 433/180 |

Primary Examiner—Cary E. O'Connor
Attorney, Agent, or Firm—Ezra L. Schacht

[57] ABSTRACT

A narrow channel is provided in an dental abutment post to allow excess dental cement to flow out of the interstitial space between the dental abutment and the overlying prosthesis. During the seating of the prosthesis the excess dental cement is channeled to and extruded from a preferred collection point for easy removal. Hydrostatic pressure and trapped gasses that would tend to lift the prosthesis into a non-fitting position or form a weakened cemented bond of uneven thickness are prevented by this apparatus and method to relieve pressure.

4 Claims, 2 Drawing Sheets

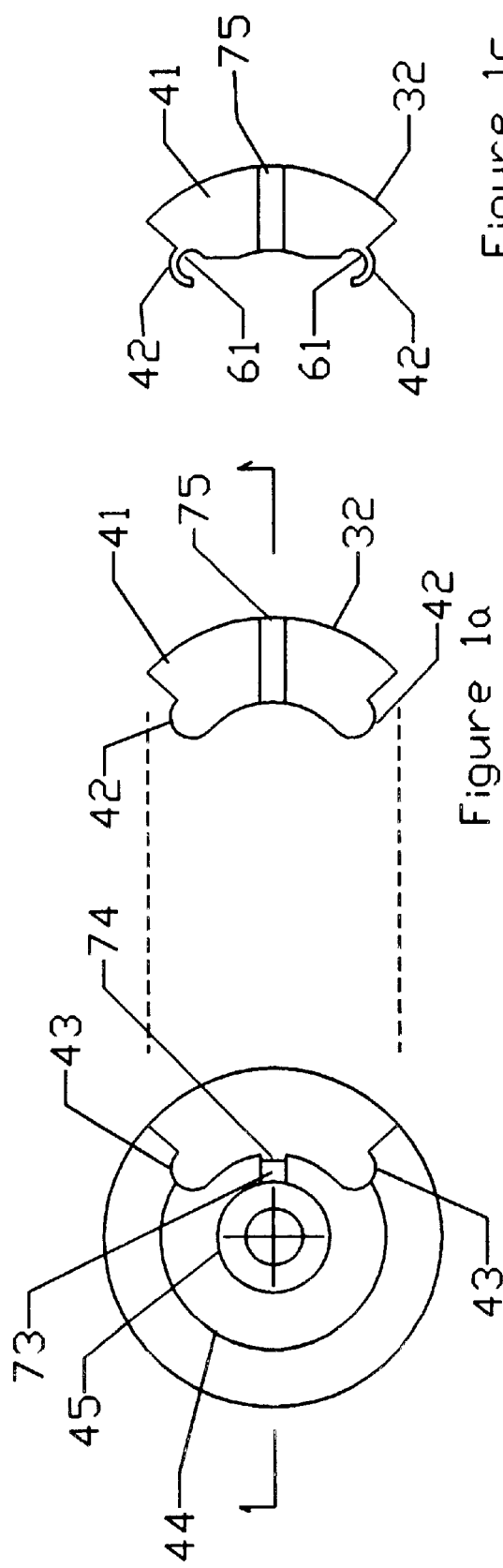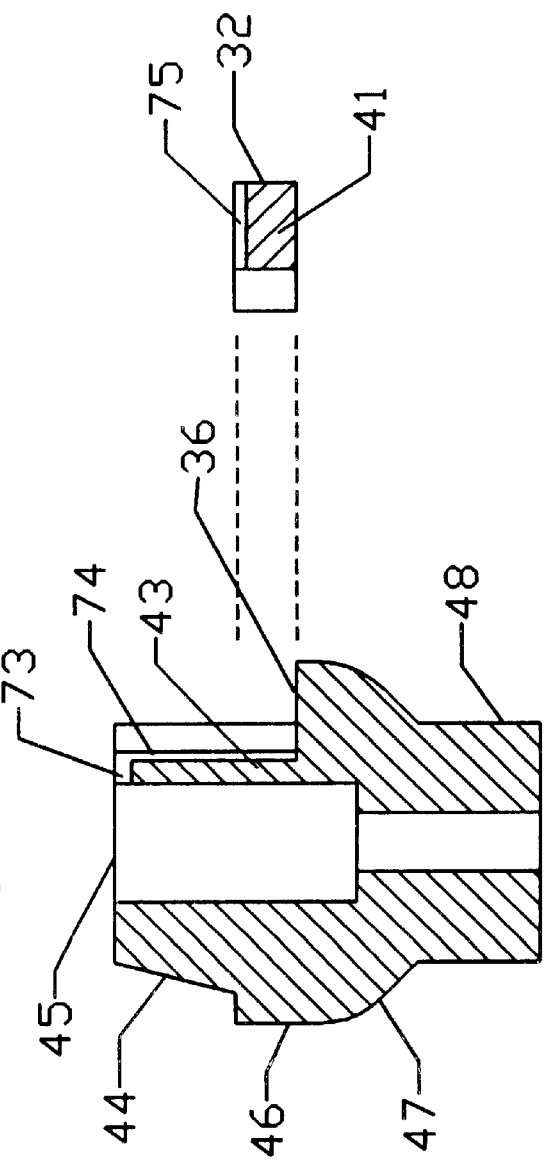

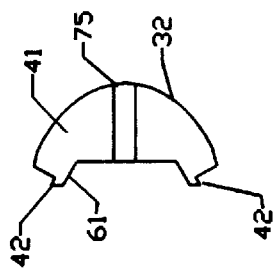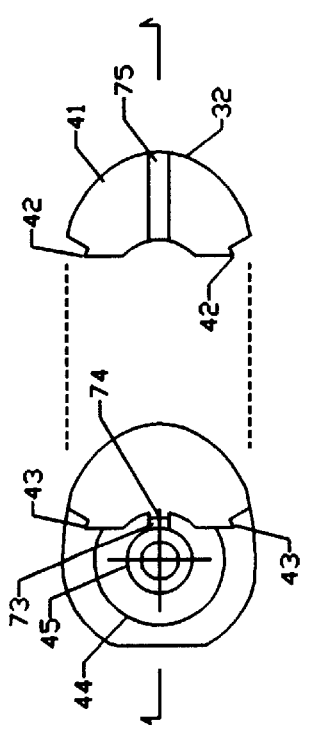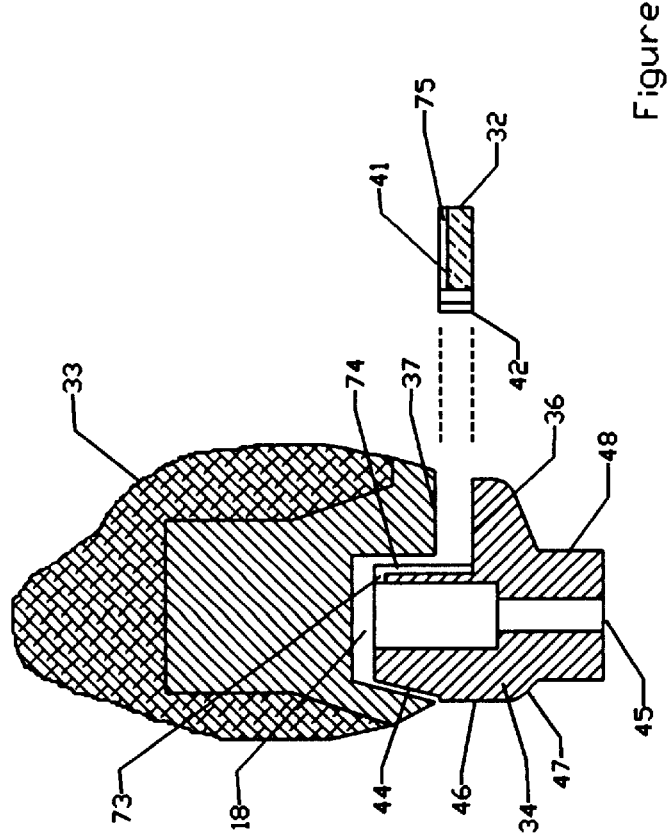

HYDROSTATIC PRESSURE RELIEVED ABUTMENT POST

CROSS REFERENCES TO OTHER APPLICATIONS

This Application is a C.I.P. of U.S. application Ser. No. 08/730,933, filed Oct. 15, 1996, pending which is a C.I.P. of U.S. application Ser. No. 08/374,933, filed Jan. 18, 1995, now allowed and issued as U.S. Pat. No. 5,564,928 on Oct. 15, 1996, and made reference herein.

BACKGROUND OF THE INVENTION

Present dental practices tend toward the replacement of lost teeth with cylindrical or plate metal alloy implants embedded in the bone of the mandible or maxilla to support the artificial tooth restoration. If extensive replacement of several teeth is needed, several implants, alone or in conjunction with existing teeth prepared as abutments, are used to anchor the replacement prosthetic teeth. As the number and complexity of support abutments are increased, the difficulty in aligning and fastening the prosthetic restoration increases. The use of several mechanically connected parts at each post or plate implant site, adds to the possibility of misalignment or biomechanical failure. The prior disclosure of the applicant in U.S. Pat. No. 5,564,928 and in pending application Ser. No. 08/730,092 describes a method and apparatus to provide a simpler mechanism and more direct technique for securing a permanently cemented, yet retrievable prosthodontic appliance while still offering a durable mechanical support.

The last two decades have led to a revolution in implant prosthodontics. Titanium alloy implant cylinders or plates are intimately installed in holes or slots drilled in the underlying bone. It is the practice to allow several months to pass while the underlying bone bonds to the surface of the implant. For this reason, implants are provided with at least one threaded hole on the crestal surface or edge. These holes are temporarily capped with a healing screw to prevent the downgrowth of soft tissue and bone into the internal threads. The soft tissue is sutured over the implant until the intimate metal-bone bond is effected.

At the next surgical encounter, the soft tissue is resected and the healing screw is replaced with a metal alloy perimucosal extension of selectable height and emergence profile and the soft tissue is sutured around the base of this extension. This extension is usually bolted in place and prevented from rotating by means of locating pins and holes or internal and external matching hexagonal (or other regular polygon shaped) projections. These perimucosal extensions form the support for artificial abutments used to support the final prosthetic restoration. The final prosthodontic restoration requires a close mechanical mating between the abutments and the matching internal aspect or underside of the prosthesis These closely matched parts often consist of telescoped, tapered cylindrical surfaces requiring a tight, non-binding, "passive" fit. This places inordinate requirements on the precision and technical skills of the dentist and the laboratory technician. Parallel alignment of the axes of each abutment to prevent binding of tapered fits cannot be easily guaranteed. The prior disclosure of the applicant in U.S. Pat. No. 5,564,928 and in pending application Ser. No. 08/730,092, relies on a conformable, cemented boundary, circumvents these objections.

Much of the current discussion in the field of dental implantology centers around the durability and maintainability of the various methods of attaching the final restoration to the underlying abutments. Bolting with threaded fasteners through the occlusal surface of the restoration and back filling with composite materials complicate the cosmetics and the retrievability of the prosthesis. Bolting through the non cosmetic, lingual side of the prosthesis has the additional requirement for a greater thickness of metal to provide mechanical support, thus reducing room for the tongue and potentially affecting speech, and the periodontal health of the abutment.

Excessive inline or rocking pressure transmitted to an individual implant from the overlying restoration may lead to frank implant failure. Failures may occur from the loosening of a screw caused by thread walking or the backing out of a screw by micro-movements. The shifting of an abutment from repetitive stresses exceeding the elastic limits between the screw thread and the internal thread of the implanted post or plate may cause the flexure or excessive loading of a single implant. Long term changes in the underlying bone structure in response to uneven stresses may lead to the loss of an individual dental implant. For each additional mechanically attached connection, alignment errors accumulate and reduce the likelihood of a good non-binding, stress free "passive" fit.

The prior disclosures of the applicant describe an apparatus and method that acts to equitably distribute the loading forces with a retrievable dental cement between the matching faces of the abutments and the internal aspect of the final restoration. Each abutment is made with at least one step or shelf on the lingual face to act as a bearing surface for a removal instrument. The final prosthesis is equipped with a flat-topped window ledge on the lingual side. There is a matching shelf on the implant abutment, with enough space between the surface of the shelf and the flat top of the window for the introduction of a wedge-tipped extraction instrument. This instrument is used to apply a prying force between each abutment and the mating ledge in the underside of the final restoration. The prying instrument applies an even opposing force between the overstructure and the abutment eliminating the potential damage to both structures. Prior methods of removing cemented restorations involved hammering movements under much less control The methods and apparatus disclosed in U.S. Pat. No. 5,564,928 in combination with an appropriate dental cement, yields a predictable technique for securing, yet retrieving the final restoration.

Furthermore, in applicants U.S. Pat. application Ser. No. 08/730,092 the "window" in the restoration is provided with a molded drop-in plug to protect against the ingress of food and to provide a smooth continuous surface to the tongue.

In advancing the art, the present invention teaches the inclusion of a groove in the surface of the implant abutment to act as a channel in the directing of excess cement from within the intervening space between the abutment and the overlying prosthesis. This channel, by allowing excess cement to flow in a controlled manner to prearranged collection site, prevents the capture of an incompressible mass of cement which will hold the overlaying prosthesis in a lifted, malocclusive position. The channel described prevents the formation of blind pockets of dental cement that would exert an outward force and weaken the joint during solidification of the dental cement.

The molded drop-in plug is likewise grooved and together with the groove formed in the abutment, forms a continuous channel for the egress of excess dental cement during the placement and alignment of the prosthesis.

BRIEF DESCRIPTION OF THE DRAWINGS

FIG. 1a displays a plan view of a grooved abutment and resilient plug with matching groove.

FIG. 1b shows an elevated cross-sectional view of the grooved abutment and matching resilient plug.

FIG. 1c shows a plan view of a grooved molded drop-in plug with a differing means of retention.

FIG. 2a displays a plan view of a grooved abutment with elongated lingual aspect.

FIG. 2b shows an elevated cross-sectional view of a grooved abutment with restoration in place.

FIG. 2c details an alternate grooved resilient plug with a different retention configuration

DETAILED DESCRIPTION OF THE DRAWINGS

In a preferred embodiment of the invention detailed in FIGS. 2a and 2b, a continuous channel formed in the abutment tapered projection 44 comprised of horizontal groove 73 and vertical groove 74. Mating groove 75 in the molded, drop-in window plug 41 provides an effective egress of dental cement from the curved outer surface 32 of the plug as the overlay prosthesis 33 is cemented in place. The molded plug 41 is captive between flat surface 37 on the bottom lingual margin of the overlay prosthesis 33 and the parallel opposed, flat surface 36 of the abutment 34.

The molded window plug projections 42 are designed to "snap" in or out of the recesses 43 between flat surfaces 36 and 37 and will provide a seal against debris. Outer curved surface 32 of the molded plug provides a tight, continuous seal with the emergence profile of the abutment 34 and overlay 33. The emergence profile, on the lingual aspect, offers a wider shelf for improved purchase of the prying tool. When prosthesis 33 is mated against the abutment tapered projection 44 excess dental cement is expressed from within gap 18 and forced along horizontal groove 73, vertical groove 74 and along horizontal groove 75 in the molded drop-in plug 41. The excess dental cement is easily removed from the surface of the lingual aspect of the seated prosthesis and plug after the cement has set.

FIG. 1c details alternate embodiments of molded drop-in plug designs with channel groove 75 Thinned sections 61 of the molded plug 41 are designed to allow projections 42 to flex into the mating recesses 43 on the abutment 34. Similar thinned sections 61 can be molded into the plug 41 detailed in FIG. 2c to allow the plug to be snapped in and out of the prying window Groove 75 is formed during the plug 41 molding process.

In FIG. 1b, the collar 46 of the abutment 34 extends through the margin of the gum with an emergence profile 47 that closely mimics that of the natural tooth. The cylindrical projection 48 makes an intimate, non-rotating mechanical connection to the underlying post implant (not shown) by means of a threaded fastener (not shown) through interior hole 45. The tapered projection 44 of the abutment is retrievably cemented to the overlay restoration 33. As an added protection against the loosening of the threaded fastener holding the abutment to the implant post, the threaded fastener is locked in place by the dental cement filling interior hole 45 and surrounding the head of the threaded fastener. Removable dental cement is used in this region.

The overlay restoration 33 is shown as a cosmetic porcelain over metal but is not limited to this composite. The window formed by flat surfaces 37 and 36, when freed of molded plug 41, provides a space for insertion of and action by a suitable prying tool to free the overlay prosthesis without damage.

The molded drop-in plug 41 can be made from a biologically acceptable plastic compound, such as one of the polymethacrylates. Projections 42 and recesses 43 can be sized to be dropped into place just prior to cementing the prosthesis in place and yet allow for removal with moderate force. The molded drop-in plug can be forced out with an appropriate tool if the plug is carefully designed and manufactured, using a durable and flexible plastic for the plug, in combination with the correct size for projections 42 and recesses 43. In FIG. 1c, projections 42 have a thinned cross section 61 to act as curved leaf springs to snap in and out of rounded recesses 43.

Another embodiment of the invention allows for the placement of a continuous channel groove in the abutment mating surface of the overlaying prosthesis with the same intention to relieve the pressure of excess dental cement by expression along said channel to an external collection area.

Whereas these drawings and descriptions shown herein for the purpose of illustrating the invention show one tooth being replaced, the method and apparatus described apply to a multiple tooth replacement site. These and other variations of the present invention may be made which fall within the scope of the appended claims even though such variations were not related above.

The accompanying drawings referred to herein are illustrative of the invention but not restrictive thereto, and, together with the description, serve to explain the principles of the invention.

What is claimed is:

1. A method of avoiding buildup of hydrostatic pressure in dental cement in the interstices between a dental abutment and the prosthesis mounted thereon, the steps of the method comprising:
    (1) creating channel means between the exterior surfaces of said abutment and adjacent said interior surfaces of said prosthesis; and
    (2) creating a venting aperture from said channel means to avoid said buildup of hydrostatic pressure
whereby misfit and lift-off of said prosthesis from said abutment as a result of said buildup of said hydrostatic pressure is avoided.

2. A dental apparatus including:
    at least one dental implant abutment, the at least one abutment having at least one flat shelf;
    at least one cementable, retrievable prosthesis, the prosthesis mating with at least one said abutment;
    said prosthesis having a flat window ledge in proximity to and parallel to at least one said flat abutment shelf, forming a gapped space of opposing surfaces for the entrance of a prying instrument to separate said prosthesis from at least one said abutment;
    said abutment having at least one continuous channel means leading from an internal portion of the dental cement filled interstices to the external surface of said prosthesis;
    said channel means allowing egress of an excess of said dental cement from said interstices to relieve hydrostatic pressure for proper seating of said prosthesis upon said abutment.

3. A dental apparatus comprising:

at least one dental implant abutment, the at least one abutment having at least one flat shelf;

a cementable, retrievable prosthesis, mating with said at least one abutment, said prosthesis having a flat window ledge in proximity to and parallel to at least one said flat abutment shelf, forming a gapped space of opposing surfaces for the entrance of a prying instrument to separate said prosthesis from at least one said abutment;

said prosthesis having at least one continuous channel leading from an internal portion of dental cement filled interstices to the external surface of said prosthesis allowing egress of excess dental cement from said interstice for proper seating of said prosthesis upon said abutment and acting to relieve pressure from trapped dental cement between said prosthesis and said abutment.

4. Apparatus for sealing a window in a dental restoration against the ingress of food particles, the dental restoration having at least one dental implant abutment, the at least one abutment having at least one flat shelf:

a cementable retrievable prosthesis, mating with said at least one abutment;

the prosthesis having at least one flat ledge in proximity to and parallel to said at least one abutment shelf, forming a gapped space of opposing surfaces for the entrance of a prying instrument;

a conformal plug insertable within said window, said plug having a smooth lingual aspect, the aspect continuous and aligned with said cemented restoration to prevent said ingress of said food particles and the concomitant development of bacterial fermentation;

the improvement comprising, in combination:

at least one continuous channel means leading from an internal portion of dental cement filled interstices to the external surface of said conformal plug allowing egress of excess dental cement from said interstices for proper seating of said prosthesis upon said abutment and acting to relieve pressure from trapped dental cement between said prosthesis and said abutment.

* * * * *